US008724884B2

United States Patent
Lomas et al.

(10) Patent No.: US 8,724,884 B2
(45) Date of Patent: May 13, 2014

(54) CONTROLLER (75) Inventors: David J. Lomas, Cambridge (GB);
Martin J. Graves, Cambridge (GB);
Daniel Peterson Godfrey, Cambridge (GB); David Seymour Warwick, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 76 days.

(21) Appl. No.: 13/576,332

(22) PCT Filed: Jan. 27, 2011

(86) PCT No.: PCT/GB2011/000105
§ 371 (c)(1),
(2), (4) Date: Jul. 31, 2012

(87) PCT Pub. No.: WO2011/092468
PCT Pub. Date: Aug. 4, 2011

(65) Prior Publication Data
US 2012/0301006 A1 Nov. 29, 2012

(30) Foreign Application Priority Data
Feb. 1, 2010 (GB) .................................. 1001626.9

(51) Int. Cl.
*G06K 9/00* (2006.01)
*A61B 1/32* (2006.01)
(52) U.S. Cl.
CPC .................. *G06K 9/00201* (2013.01)
USPC .......................... 382/153; 600/228
(58) Field of Classification Search
USPC ....................................................... 382/153
See application file for complete search history.

(56) References Cited

U.S. PATENT DOCUMENTS 4,884,216 A * 11/1989 Kuperstein ..................... 700/259
5,579,444 A * 11/1996 Dalziel et al. ................. 700/259
(Continued)

FOREIGN PATENT DOCUMENTS

| GB | 2347199 | 8/2000 |
| WO | 2006/066401 | 6/2006 |
| WO | 2008/084232 | 7/2008 |

OTHER PUBLICATIONS

Debbins et al, Cardiac Magnetic Resonance Fluoroscopy, Magn. Reson. Med. (MRM) 36, 1996, pp. 588-595.
(Continued)

*Primary Examiner* — Alex Liew
(74) *Attorney, Agent, or Firm* — Stepehen H. Eland; Dann, Dorfman, Herrell & Skillman (57) ABSTRACT

A controller is provided for maneuvering an interrogation plane relative to a reference surface. The interrogation plane intersects the reference surface and is associated with a pole about which the interrogation plane is rotatable. The pole has an adjustable angle of inclination relative to the reference surface. The controller has a base, a handle, and an arm extending from a connection with the base to a connection with the handle. The arm has hingable joints which hinge to allow the handle to be translated relative to the base in arbitrary directions across a user surface. The controller further has position sensors which measure the translation of the handle relative to the base on the user surface. The translation provides a corresponding translation of the interrogation plane relative to the reference surface. The handle is rotatable about a rotation axis and is tillable about a tilt axis to allow the handle to be angularly moved relative to the user surface. The controller further has angle sensors which respectively detect the rotation about the rotation axis and the tilt about the tilt axis. The rotation about the rotation axis and the tilting about the tilt axis provide angular movement of the interrogation plane relative to the reference surface corresponding to the angular movement of the handle relative to the user surface.

14 Claims, 3 Drawing Sheets

(56) References Cited

U.S. PATENT DOCUMENTS

| | | | |
|---|---|---|---|
| 5,701,140 A * | 12/1997 | Rosenberg et al. | 345/156 |
| 5,727,668 A * | 3/1998 | Demarest et al. | 198/431 |
| 6,333,631 B1 * | 12/2001 | Das et al. | 324/326 |
| 6,611,617 B1 * | 8/2003 | Crampton | 382/154 |
| 6,642,922 B1 * | 11/2003 | Noda | 345/419 |
| 6,905,823 B2 * | 6/2005 | Kallioniemi et al. | 435/6.14 |
| 7,313,264 B2 * | 12/2007 | Crampton | 382/154 |
| 2003/0109857 A1 | 6/2003 | Sanchez et al. | |
| 2003/0152261 A1 * | 8/2003 | Hiroe et al. | 382/153 |
| 2003/0230723 A1 * | 12/2003 | Garrard et al. | 250/363.1 |
| 2005/0177054 A1 * | 8/2005 | Yi et al. | 600/510 |
| 2007/0032720 A1 | 2/2007 | Koivukangas et al. | |
| 2007/0076946 A1 * | 4/2007 | Kunisaki et al. | 382/153 |
| 2012/0301006 A1 * | 11/2012 | Lomas et al. | 382/131 |

OTHER PUBLICATIONS

Graves et al, Constrained Surface Controllers for Three-Dimensional Image Data Reformatting, Radiology, vol. 252, No. 1, Jul. 2009, pp. 218-224.

Stainsby et al, Integrated Real-Time MRI User-Interface, Proc. Intl. Soc. Magn. Reson. Med. (MRM) 11, 2004, p. 537.

Hardy et al, Interactive Coronary MRI, Magn. Reson. Med. (MRM) 40, 1998, pp. 105-111.

Yi et al, Intuitive and Efficient Control of Real-Time MRI Scan Plane Using a Six-Degree-of-Freedom Hardware Plane Navigator, Medical Image Computing and Computer-Assisted Intervention MICCAI, vol. 3217, 2004, pp. 430-437.

Kerr et al, Real-Time Interactive MRI on a Conventional Scanner, Magn. Reson. Med. (MRM) 38, 1997, pp. 355-367.

* cited by examiner

CONTROLLER

FIELD OF THE INVENTION

The present invention relates to a controller for maneuvering an interrogation plane relative to a reference surface. For example, the controller can manoeuvre the interrogation plane through volumetric data relative to the reference surface.

BACKGROUND OF THE INVENTION

MRI (magnetic resonance imaging) or X-ray CT (X-ray computerised tomography) can be used both to provide sectional views of a body in real-time and to generate volumetric data (i.e. 3D data) corresponding to a body for later interrogation. Often the volumetric data is interrogated to provide displayable sectional views of the body.

The sectional view can be generated anywhere within the volumetric data. Indeed, some systems give the user a sensation that the sectional view can be freely moved (or "navigated") through the volumetric data. However, navigating the sectional view through the volumetric data can prove difficult and disorientating to a user.

For example, in conventional MRI or CT systems, graphical user interface (GUI) interactions allow the user to adjust one or more parameters of the sectional view to navigate the sectional view through the volumetric data. Conventional techniques of adjustment often employ mouse and GUI based methods for determining the location of the image plane containing the sectional view. Examples of techniques include: line drawing (Kerr A B et al., Magn Reson Med 1997; 38; p. 355-367); placing points (Debbins J P et al., Magn Reson Med 1996; 36; p. 588-595); and selecting reference icons (Hardy C J et al., Magn Reson Med 1998; 40; p. 105-111). However, the need for the user to manually adjust these parameters often distracts attention from the displayed sectional view of the volumetric data. This is undesirable when interrogating sectional views of MRI or CT generated volumetric data of e.g. a human subject's body, because abnormalities in the subject's anatomy can easily be overlooked.

In an attempt to overcome the need for the user to divert attention away from the displayed sectional view towards the one or more parameter adjustment GUIs, specialized controllers have been proposed, which allow the user generally to remain focussed on the output image. Such controllers typically provide 6 degrees of freedom (DOF) of image plane control so that the corresponding sectional view remains freely navigatable through the volumetric data. Examples of the 6 DOF controllers are the "spaceball" (Hardy C J, et al. Magn Reson Med 1998; 40; p. 105-111), the 3 DOF and 6 DOF mice (Hardy C J, et al. Magn Reson Med 1998; 40; p. 105-111) and the robotic arm (Yi D, et al., Medical Image Computing and Computer-Assisted Intervention MICCAI 2004, vol. 3217, pp. 430-437, 2004).

However, these controllers can rapidly disorientate the user because the image plane (in which the displayed sectional view is generated) is freely movable through the volumetric data. Consequently, a user may have to re-orientate himself in the volumetric data by re-starting the navigation of the image plane from a known location in a known orientation.

It has been proposed that the relative position of the freely movable image plane, in which the sectional view is generated, should be mapped on the volumetric data itself and displayed to the user, thereby providing visual feedback to the user as to the relative position of the image plane with respect to the volumetric data (Hardy C J, et al. Magn Reson Med 1998; 40; p. 105-111 and Stainsby et al., PROC ISMRM 2004: 537). Such feedback is sometimes referred to as image plane tracking. However, the visual feedback still requires the operator to divert attention from the displayed sectional view(s) in order to determine the location of the image plane with respect to the volumetric data. This again creates user distraction, which is undesirable.

The above discussion is mainly directed at the interrogation of volumetric image data. However, the problems associated with navigating volumetric image data using the conventional methods and systems also exist when interrogating a body in real-time, e.g. by MRI or X-ray CT.

WO2008/084232 proposes a method of interrogating volumetric data including the steps of: (i) defining a reference surface relative to the volumetric data; (ii) providing an interrogation window lying in a movable interrogation plane intersecting the reference surface and the interrogation window intersecting the volumetric data, wherein translation and/or rotation of the interrogation plane provides a corresponding movement of the interrogation window; (iii) the interrogation plane being associated with a pole about which pole said interrogation plane is rotatable, and for each movement of the interrogation plane, determining the point of intersection of the pole and the reference surface, determining the relative angle of rotation of the interrogation plane about the pole and determining the angle of inclination of the pole to the reference surface; and (iv) on the basis of the determinations in step (iii), providing a sectional image through the volumetric data corresponding to the position of the interrogation window within the volumetric data. WO2008/084232 also proposes a corresponding method of controlling an imaging apparatus to acquire a sectional image of a body.

The approach of WO2008/084232 is based on an appreciation that that the different diagnostic field of real-time 2D ultrasound scanning has important features lacking in conventional computer implemented data interrogation methods and control systems. Thus, in real-time 2D ultrasound scanning, a sectional view of an appropriate subject can be generated and the image plane (containing the sectional view) can be moved freely through the body. However, here the sonographer uses a combination of their knowledge of the subject's internal anatomy and of tactile and spatial cues from the hand manipulating the ultrasound transducer to move the image plane in a controllable, predictable and "automatic" or intuitive way. The sonographer can therefore focus on the sectional view of the subject provided on a display. It is not necessary to use other means, such as mouse/controller/GUIs, in order to establish where the image plane is located in the subject, i.e. image plane tracking feedback is not required. Further discussion of the approach is provided in Graves M J, et al., Radiology 2009; 252; p. 218-224.

WO2008/084232 and Graves M J, et al., Radiology 2009; 252; p. 218-224 propose prototype controllers for maneuvring the interrogation plane with respect to the reference surface. However, these controllers are bulky and/or relatively complicated which may hinder their widespread uptake and consequently the adoption of the methods of WO2008/084232.

SUMMARY OF THE INVENTION

Accordingly, the present invention aims to provide an alternative controller for use in the methods of WO2008/084232, the controller overcoming or avoiding problems associated with known controllers.

Thus, in a first aspect the present invention provides a controller for maneuvring an interrogation plane relative to a reference surface, the interrogation plane intersecting the reference surface and being associated with a pole about which the interrogation plane is rotatable, the pole having an adjustable angle of inclination relative to the reference surface, the controller having:

a base, a handle, an arm extending from a connection with the base to a connection with the handle, the arm having hingable joints which hinge to allow the handle to be translated relative to the base in arbitrary directions across a user surface, and position sensors which measure the translation of the handle relative to the base on the user surface, the translation providing a corresponding translation of the interrogation plane relative to the reference surface;

wherein the handle is rotatable about a rotation axis and is tiltable about a tilt axis to allow the handle to be angularly moved relative to the user surface, the controller further having angle sensors which respectively detect the rotation about the rotation axis and the tilt about the tilt axis, and the rotation about the rotation axis and the tilting about the tilt axis providing angular movement of the interrogation plane relative to the reference surface corresponding to the angular movement of the handle relative to the user surface.

Advantageously, the controller can provide absolute positioning (both translational and angular) of the handle relative to the base and user surface, and hence of the interrogation plane relative to the reference surface. The controller can also be made simple, compact, accurate and robust.

The controller may have any one, or to the extent that they are compatible, any combination of the following optional features.

Typically, the interrogation plane only has 5 DOF with respect to the reference surface such that the interrogation plane is not controllable to translate in a direction normal to the point of intersection of the pole and reference surface, e.g. normal to the reference surface. Preferably, the interrogation plane only has 4 DOFs with respect to the reference surface, i.e. two degrees of translational freedom across the reference surface, and two degrees of rotational freedom.

Conveniently, the user surface is planar. For example, it can be a desk or table top.

Typically, the arm is configured such that the handle is constrained to translate relative to the base only across the user surface. That is, the handle typically has only two translational DOFs. In this way, the user can avoid being disorientated, as the interrogation plane is not freely movable through volumetric data. The constraint can provide an experience for the user similar to that of performing real-time 2D ultrasound scanning.

Typically, the handle has only two rotational DOFs, i.e. rotation about the rotation axis and tilt about the tilt axis.

Preferably, the tilt axis is parallel to the user surface. Preferably the tilt axis is rotated by rotation of the handle about the rotation axis. The tilt axis may thus correspond to the line of intersection of the reference surface and the interrogation plane. Tilting about the tilt axis may provide a corresponding change in the angle of inclination of the pole relative to the reference surface.

Preferably the rotation axis is perpendicular to the user surface. The rotation axis may thus correspond to the pole only when the pole is perpendicular to the reference surface. Nonetheless, any angular position of the interrogation plane relative to the reference surface can be arrived at by a combination of a rotation of the interrogation plane about the pole when the pole is perpendicular to the reference surface followed by an inclination of the pole about the line of intersection of the interrogation plane and the reference surface. Thus rotation of the handle about the rotation axis can provide corresponding angular movement of the interrogation plane relative to the reference surface. Further, the rotation of the handle can be encoded as a corresponding rotation of the interrogation plane about the pole when angular position of the interrogation plane relative to the reference surface is defined as rotation of the interrogation plane about the pole when the pole is perpendicular to the reference surface followed by inclination of the pole about the line of intersection of the interrogation plane and the reference surface.

Preferably the arm has a hingable joint at the connection with the base and has a further hingable joint at a position between the connection with the base and the connection with the handle.

The arm may have an arm support pad at the further hingable joint, the arm support pad supporting the arm on the user surface. Likewise, the arm may have a support pad at the connection with the handle, the support pad supporting the handle on the user surface. For example, the, or each, support pad can be formed of PTFE pad for low wear and low sliding resistance on the user surface.

The handle can rotate about the rotation axis at the connection with the arm. The handle can tilt about the tilt axis at the connection with the arm. This allows a compact controller to be achieved.

Conveniently, the position sensors may detect the hinge angles of the hingable joints, the translation of the handle relative to the base on the user surface being determined from the hinge angles. That is, the position sensors can provide an indirect measure of the handle translation from the hinge angles, some processing of the hinge angles being required to arrive at the handle translation.

A second aspect of the invention provides a method of maneuvering an interrogation plane relative to a reference surface, the interrogation plane intersecting the reference surface and being associated with a pole about which the interrogation plane is rotatable, the pole having an adjustable angle of inclination relative to the reference surface, the method comprising:

positioning a controller according to the first aspect on a user surface such that the handle rests on the user surface, and translating the handle relative to the base across the user surface, rotating the handle about the rotation axis, and/or tilting the handle about the tilt axis in order to translate the interrogation plane relative to the reference surface, and/or angularly move the interrogation plane relative to the reference surface.

A third aspect of the invention provides a computer system for interrogating volumetric data, the computer system having one or more processors configured to perform the steps of:

(i) defining a reference surface relative to the volumetric data, (ii) providing an interrogation window lying in a movable interrogation plane intersecting the reference surface and the interrogation window intersecting the volumetric data, wherein translation and/or rotation of the interrogation plane provides a corresponding movement of the interrogation window, (iii) determining the point of intersection of a pole and said reference surface, said interrogation plane being associated with and rotatable about said pole, and for each movement of the interrogation plane, determining a relative angle of rotation of said interrogation plane about said pole and determining the angle of inclination of said pole to said reference surface, and (iv) on the basis of said determinations in step (iii), providing a sectional image through the volumetric data corresponding to the relative position and orientation of the interrogation window within the volumetric data;

wherein the computer system further has a controller according to the first aspect for maneuvring in use said interrogation plane with respect to the reference surface.

A fourth aspect of the invention provides a computer system for controlling an imaging system to provide a sectional image of a body, the computer system having one or more processors configured to perform the steps of:

(i) defining a reference surface corresponding to a control surface having a pre-determined relationship with the body, with respect to which control surface a sectional image through a particular portion of the body is generatable by the imaging system, (ii) providing an interrogation window lying in a movable interrogation plane intersecting the reference surface, wherein translation and/or rotation of the interrogation plane provides a corresponding movement of the interrogation window, (iii) determining the point of intersection of a pole and said reference surface, said interrogation plane being associated with and rotatable about said pole, and for each movement of the interrogation plane, determining a relative angle of rotation of said interrogation plane about said pole and determining the angle of inclination of said pole to said reference surface, and (iv) on the basis of said pre-determined relationship and said determinations in step (iii), providing a sectional image through the body, the sectional image corresponding to the relative position and orientation of the interrogation window to the reference surface;

wherein the computer system further has a controller according to the first aspect for maneuvring in use said interrogation plane with respect to the reference surface.

In the third and fourth aspects, the determination of a relative angle of rotation of said interrogation plane about said pole is typically performed with the pole perpendicular to the reference surface. Determining the angle of inclination of said pole to said reference surface is typically then performed as a subsequent step.

The computer system of the third or fourth aspect may further include a visual display for displaying the sectional image.

BRIEF DESCRIPTION OF THE DRAWINGS

Embodiments of the invention will now be described by way of example with reference to the accompanying drawings in which:

FIGS. 6(a) and (b) show just the handle of the controller of FIG. 1.

DETAILED DESCRIPTION

A computer can be used to generate sectional images (e.g. on a visual display unit) of volumetric data, e.g. acquired by or generated as a result of MRI or X-ray CT, to allow a user to interrogate the volumetric data. Using the approach of WO2008/084232, the plane in which the sectional image lies intersects a pre-determined reference surface. The reference surface may lie proximate to the volumetric data, or it may lie in the volumetric data. The reference surface is preferably planar, but it could be a curved surface, e.g. a spherically or cylindrically curved surface.

The computer provides an image (or interrogation) window which lies in an interrogation plane. When the interrogation window at least partly lies within the volumetric data, the computer may provide a sectional image through the volumetric data corresponding to the interrogation window's position within the volumetric data.

The interrogation plane is preferably movable with respect both to the volumetric data and to the reference surface, although the interrogation plane is required to intersect the reference plane (it is also conceivable that the interrogation plane could lie completely within the reference surface, e.g. where the reference surface is planar, and so it is intended that by intersect, coexistence is also meant). Movement of the interrogation plane produces a corresponding movement of the interrogation window.

A pole may intersect or extend parallel to the interrogation plane, but it preferably lies in the interrogation plane. The interrogation plane, and therefore the interrogation window is rotatable about the pole to provide different sectional images of the volumetric data. The pole (and therefore the interrogation plane and window) is tiltable with respect to the reference surface thereby varying the angle between the pole and the reference surface to provide different sectional images of the volumetric data. Indeed, the point of intersection of the pole and the reference surface is translatable across the reference surface (and therefore the interrogation plane and window are translatable with respect to the reference surface) to provide different sectional images of the volumetric data.

For each movement of the interrogation plane, e.g. by a user controlling the interrogation plane to move, the computer determines the new position of the interrogation window and therefore can provide a new sectional image through the volumetric data, corresponding to the position of the interrogation window in the volumetric data.

The reference surface is in a predetermined position relative to the volumetric data, and the interrogation plane intersects the reference surface. So, the position of the interrogation plane relative to the volumetric data can be determined by the arrangement of the interrogation plane and the reference surface. Therefore, the extent of rotation of the interrogation plane about the pole is determined, the point of intersection of the reference surface and the pole is determined and the angle of inclination of the pole to the reference surface is determined, thereby determining the mutual arrangement of the interrogation plane and the reference surface. Once this arrangement is determined the computer can generate a new sectional image for display on e.g. a visual display unit.

Even if the reference surface is movable with respect to the volumetric data, the computer can determine the (changing) relationship between the reference surface and the volumetric data and determine the position of the interrogation window accordingly and therefore determine the position of the interrogation window with respect to the volumetric data and generate a sectional image of the volumetric data if appropriate. However, the interrogation plane may only have 5 DOF with respect to the reference surface such that the interrogation plane is not controllable to translate in a direction normal to the point of intersection of the pole and reference surface, e.g. normal to the reference surface. Preferably, the interrogation plane only has 4 DOFs with respect to the reference surface, i.e. two degrees of translational freedom across the reference surface, and two degrees of rotational freedom.

Whilst the above description is directed to the interrogation of volumetric data, e.g. volumetric image data acquired by MRI or X-ray CT of a body, the approach of WO2008/084232 is also suitable for real-time MRI.

For example, a computer may implement a method according to the approach of WO2008/084232 to control an imaging system to generate sectional images of a body. Under the control of a computer, the imaging system may be capable of generating a sectional image arbitrarily through the body, with respect to a control surface (e.g. acting as a reference frame) which has a pre-determined relationship with the body. The computer may define a reference surface corresponding to the control surface and it may define an interrogation plane and window as above, thereby providing the user with the advantages outlined above.

In response to a movement of the interrogation window relative to the reference surface e.g. by a user, the imaging system may generate a sectional image of the body in a portion of the body relative to the control surface corresponding to the position and orientation of the interrogation window relative to the reference surface.

FIGS. 1 to 5 show respectively side, end, top, left perspective and right perspective views of a controller, according to the present invention, for maneuvering the interrogation plane with respect to the reference surface. The controller provides equivalents of the interrogation plane and reference surface generated by the computer (albeit scaled up or down in size as desired). The block arrows in FIGS. 3 and 4 indicate the motions allowed by the handle.

The controller includes a base 10, a handle 12 and an arm 14 extending from a hinged joint connection 16 with the base to an end connection 18 with the handle. The arm has a further hinged joint 20 midway between the connections 16, 18. Hinged joint 16 allows about 150° of rotation about its hinge axis, and hinged joint 20 allows about 170° of rotation about its hinge axis. Articulation of the hinged joints thus allows the handle to be translated over a user surface, such as a table or desk top, on which the controller is positioned. However, the construction of the hinged joints prevents the handle from being translated in directions which are not parallel with the plane of the user surface. The midway hinged joint has a PTFE pad 22 which supports the arm on the user surface while providing low resistance to sliding. Likewise, the end connection has a PTFE pad 24 which supports the handle on the user surface while providing low resistance to sliding.

The end connection 18 has a rotation joint 26 which provides about 445° of rotation of the handle 12 about a normal 30 to the user surface through the centre of the end connection. In this way, irrespective of handle translation position, about 270° useful rotation of the handle is always available to the user. The end connection also has a tilt joint 32 which provides ±90° of tilt of the handle about a tilt axis 34 extending parallel to the user surface, the tilt axis being rotated with the handle about the normal. Thus, with respect to the end connection, the handle only has 2 DOF, namely rotation about the normal and tilt about the tilt axis.

Each hinged joint 16, 20 has an angle encoder which measures the hinge angle of the joint. The signals from these encoders are sent to the base 10 and to a connector 38, such as a universal serial bus, at the rear of the base. Some processing of the signals may be performed before the signals arrive at the connector. From here the signals can be sent to the computer and converted into a translation of the handle 12 relative to the base on the user surface. This in turn corresponds to a translation of the interrogation plane relative to the reference surface.

Although the handle 12 is constrained to translate across the user surface, it is helpful to conceive of the controller as providing a constraint surface for translation of the handle which is parallel to the user surface and contains the tilt axis 34. The constraint surface, which is thus offset from the user surface, corresponds to the reference surface.

Figure 1:
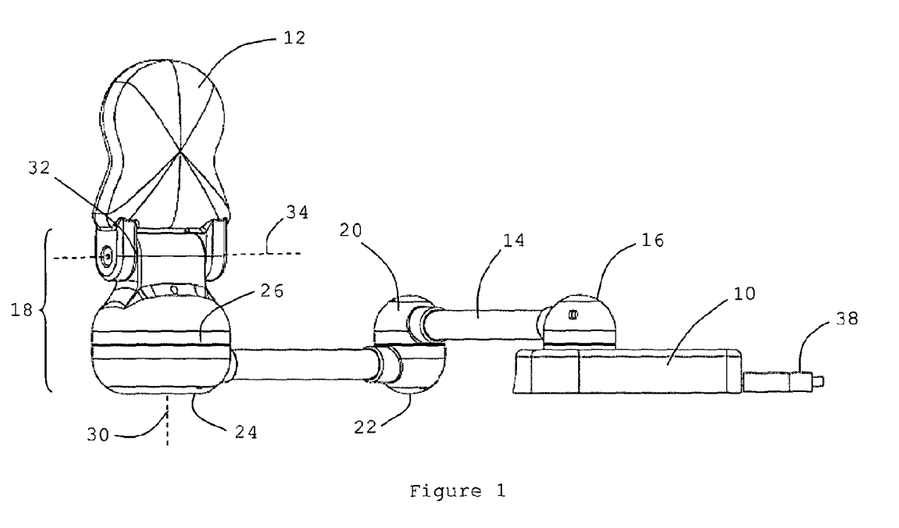
FIG. 1 shows a side view of a controller according to the present invention.
Figure 2:
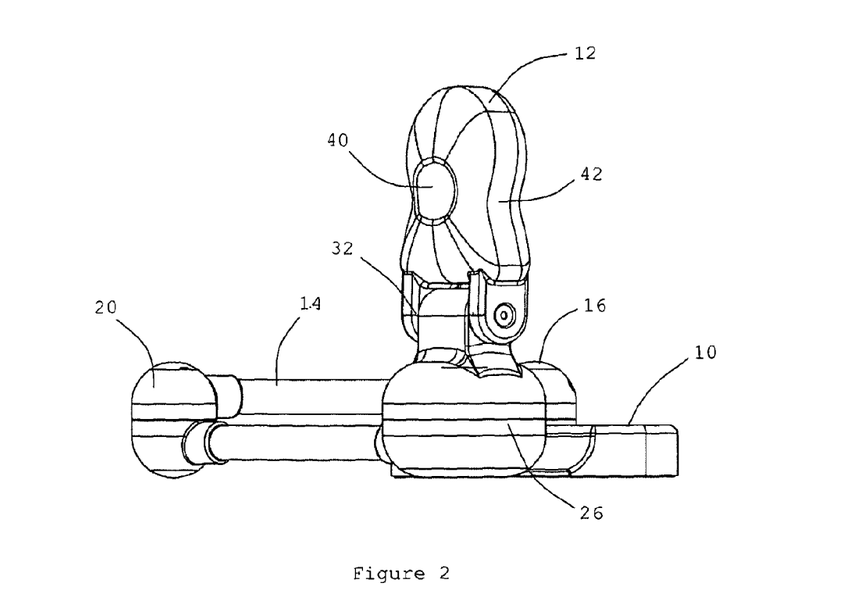
FIG. 2 shows an end view of the controller of FIG. 1.
Figure 3:
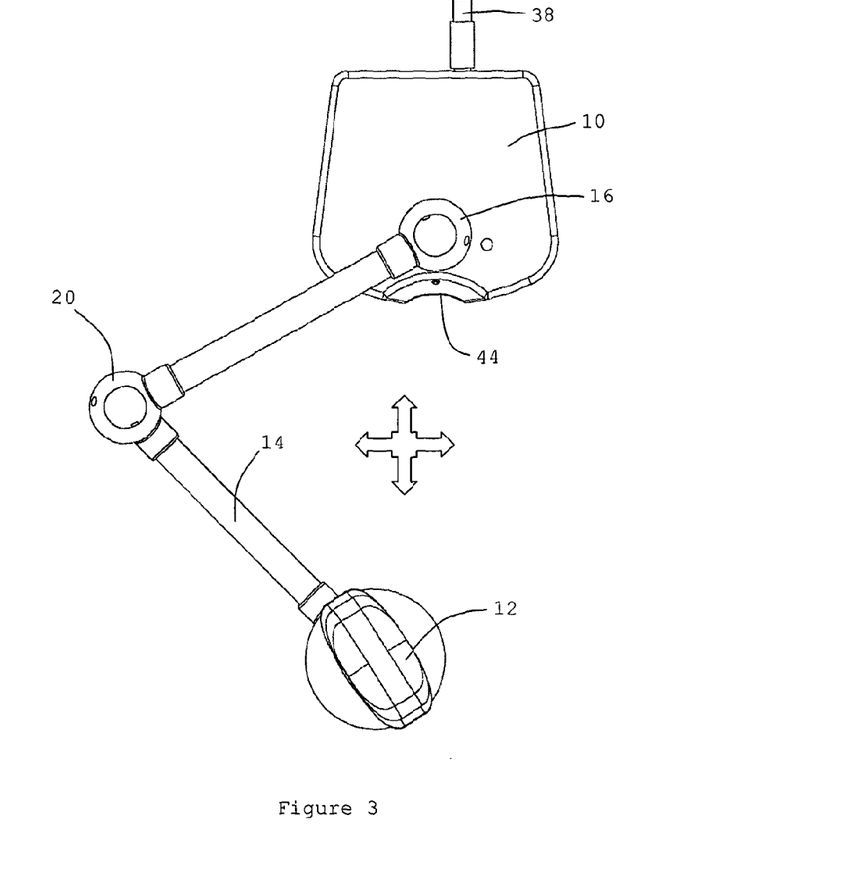
FIG. 3 shows a top view of the controller of FIG. 1.
Figure 4:
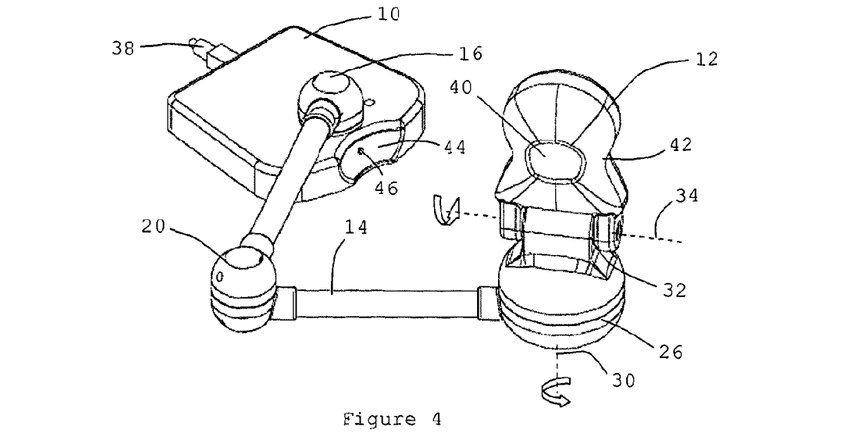
FIG. 4 shows a left perspective of the controller of FIG. 1.
Figure 5:
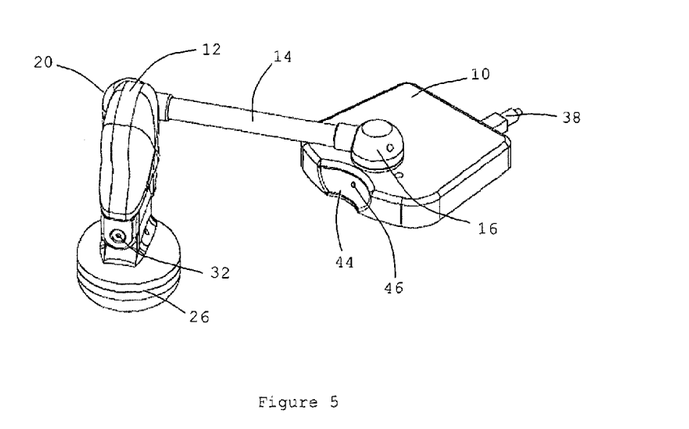
FIG. 5 shows a right perspective of the controller of FIG. 1.
Figure 6:
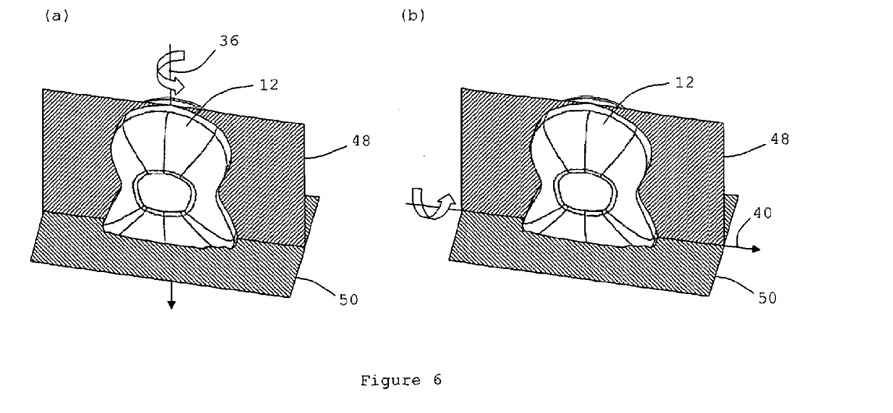

The handle 12 is essentially planar (i.e. it is wider and longer than it is thick), the position of the plane of the handle in relation to the constraint surface corresponding to the position of the interrogation plane in relation to the reference surface. The handle alone is shown in FIG. 6(a) in relation to the pole 36 of the interrogation plane 48, and in FIG. 6(b) in relation to the line of intersection 40 of the interrogation plane with the reference surface 50, the pole being inclinable to the reference surface about the line of intersection.

The line of intersection 40 always coincides with the axis 34 of the tilt joint 32. Further, the tilt angle of the tilt joint is the same as the angle of inclination of the pole 36 relative to the reference surface 50. In contrast, the pole 36 only coincides with the axis 30 of the rotation joint 26 when the handle is in its upright position (i.e. zero tilt), as shown in FIG. 6(a). Nonetheless, for any rotation of the handle about the rotation joint, the corresponding angular movement of the interrogation plane 48 relative to the user surface can be determined from the angular positions of the tilt joint and the rotation joint.

The rotation joint 26 and the tilt joint 32 have respective angle encoders which measure the rotation and tilt angles of the joints. The signals from these encoders are sent down the arm 14 to the connector 38 (with optional processing before arriving at the connector), and thence to the computer. Here they are converted into a rotation of the interrogation plane 48 about the pole 36 when the pole is perpendicular to the reference surface 50 followed by an inclination of the interrogation plane relative to the reference surface. This combination of angular movements angularly positions the interrogation plane relative to the reference surface in correspondence with the angular position of the handle relative to the constraint surface.

The combination of the rotation joint 26 and the tilt joint 32 thus permits the user to arrange the plane of the handle 12 at any oblique angle to (or to be perpendicular to) the constraint surface. Further, as discussed above, translating the handle 12 over the constraint surface produces a corresponding translation of the interrogation plane 48 over the reference surface 50. For any position of the handle, the computer can therefore determine a corresponding arrangement of the interrogation plane and the reference surface, in order to be able to display a sectional image corresponding to the position of the interrogation window within the interrogation plane. When the handle and hence the interrogation plane move, the display is updated to show the sectional image corresponding to the next position of the interrogation window.

Constraining the movement of the handle 12 to the two translational DOFs (provided by hinged joints 16, 20) and the two rotational DOFs (provided by the rotation axis 30 and the tilt axis 34) provides an experience to the user of moving the interrogation plane 48 through volumetric data over the reference surface 50 which is akin to the performance of real-time 2D ultrasound scanning where the ultrasound scanner is moved over a external surface of the subject. Maneuvering the interrogation plane can thus become intuitive, allowing the user to focus on the display in the interrogation window rather than on moving the interrogation plane. In this way the controller facilitates the rapid location of complex oblique planes in previously acquired volumetric data sets (obtained by e.g. 3D MRI, multiple contiguous slice 2D MRI, or multi-detector helical X-ray CT) corresponding to the mutual arrangement of the handle and the constraint surface. A user wishing to interrogate volumetric image data can easily navigate the interrogation plane through the data without becoming disorientated.

The controller can also be interfaced to an MRI system whereby the controller provides the geometry coordinates for the interrogation window in such a way that the MRI system obtains a 2D image at the corresponding location within the magnet bore in which a subject is positioned. By using fast acquisition methods such as balanced or spoiled gradient echo sequences, for example, real-time MRI is possible and the controller permits the interactive positioning of the interrogation window within the subject to acquire a sectional image.

The articulated arm 14 of the controller provides smooth movement of the handle 12, while also facilitating a convenient and accurate means of measuring absolute translational position and angular orientation via the angle encoders. The controller is also robust, stable and relatively compact.

To enhance ergonomics, the handle 12 has a thumb depression 40 on one face and recesses 42 at opposing sides for improved grip. The base 10 also has a recess 44 for docking the end connection 18 when the controller is not in use. A switch 46, which resets the translational position of the handle 12, is located in the recess and is activated when the end connection is docked. The base 10 is relatively massive to prevent the base sliding on the user surface during use of the controller.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references mentioned above are incorporated by reference.

The invention claimed is:

1. A controller for maneuvering an interrogation plane relative to a reference surface, the interrogation plane intersecting the reference surface and being associated with a pole about which the interrogation plane is rotatable, the pole having an adjustable angle of inclination relative to the reference surface, the controller having:
   a base,
   a handle,
   an arm extending from a connection with the base to a connection with the handle, the arm having hingable joints which hinge to allow the handle to be translated relative to the base in arbitrary directions across a user surface, and
   position sensors which measure the translation of the handle relative to the base on the user surface, the translation providing a corresponding translation of the interrogation plane relative to the reference surface;
   wherein the handle is rotatable about a rotation axis and is tiltable about a tilt axis to allow the handle to be angularly moved relative to the user surface, the controller further having angle sensors which respectively detect the rotation about the rotation axis and the tilt about the tilt axis, and the rotation about the rotation axis and the tilting about the tilt axis providing angular movement of the interrogation plane relative to the reference surface corresponding to the angular movement of the handle relative to the user surface;
   wherein the arm is configured such that the handle is constrained to translate relative to the base only across the user surface; and
   wherein the arm has a support pad at the connection with the handle, the support pad supporting the handle on the user surface.

2. A controller according to claim 1, wherein the handle has rotational degrees of freedom only through rotation about the rotation axis and tilt about the tilt axis.

3. A controller according to claim 1, wherein the tilt axis is parallel to the user surface.

4. A controller according to claim 1, wherein the tilt axis is rotated by rotation of the handle about the rotation axis.

5. A controller according to claim 1, wherein the rotation axis is perpendicular to the user surface.

6. A controller according to claim 1, wherein the arm has a hingable joint at the connection with the base and has a further hingable joint at a position between the connection with the base and the connection with the handle.

7. A controller according to claim 6, wherein the arm has an arm support pad at the further hingable joint, the arm support pad supporting the arm on the user surface.

8. A controller according to claim 1, wherein the handle rotates about the rotation axis at the connection with the arm.

9. A controller according to claim 1, wherein the handle tilts about the tilt axis at the connection with the arm.

10. A computer controller according to claim 1, wherein the position sensors measure the hinge angles of the hingable joints, the translation of the handle relative to the base on the user surface being determined from the hinge angles.

11. A method of maneuvering an interrogation plane relative to a reference surface, the interrogation plane intersecting the reference surface and being associated with a pole about which the interrogation plane is rotatable, the pole having an adjustable angle of inclination relative to the reference surface, the method comprising the steps of:
   positioning a controller according to claim 1 on a user surface such that the handle rests on the user surface, and translating the handle relative to the base across the user surface, rotating the handle about the rotation axis, and/or and tilting the handle about the tilt axis in order to respectively translate the interrogation plane relative to the reference surface, and/or angularly move the interrogation plane relative to the reference surface.

12. A computer system for interrogating volumetric data, the computer system having one or more processors configured to perform the steps of:
   (i) defining a reference surface relative to the volumetric data,
   (ii) providing an interrogation window lying in a movable interrogation plane intersecting the reference surface and the interrogation window intersecting the volumetric data, wherein translation and/or rotation of the interrogation plane provides a corresponding movement of the interrogation window,
   (iii) determining the point of intersection of a pole and said reference surface, said interrogation plane being associated with and rotatable about said pole, and for each movement of the interrogation plane, determining a relative angle of rotation of said interrogation plane about said pole and determining the angle of inclination of said pole to said reference surface, and
   (iv) on the basis of said determinations in step (iii), providing a sectional image through the volumetric data corresponding to the relative position and orientation of the interrogation window within the volumetric data;

wherein the computer system further has a controller according to claim 1 for maneuvering in use said interrogation plane with respect to the reference surface.

13. A computer system for controlling an imaging system to provide a sectional image of a body, the computer system having one or more processors configured to perform the steps of:
(i) defining a reference surface corresponding to a control surface having a pre-determined relationship with the body, with respect to which control surface a sectional image through a particular portion of the body is generatable by the imaging system,
(ii) providing an interrogation window lying in a movable interrogation plane intersecting the reference surface, wherein translation and/or rotation of the interrogation plane provides a corresponding movement of the interrogation window,
(iii) determining the point of intersection of a pole and said reference surface, said interrogation plane being associated with and rotatable about said pole, and for each movement of the interrogation plane, determining a relative angle of rotation of said interrogation plane about said pole and determining the angle of inclination of said pole to said reference surface, and
(iv) on the basis of said pre-determined relationship and said determinations in step (iii), providing a sectional image through the body, the sectional image corresponding to the relative position and orientation of the interrogation window to the reference surface;

wherein the computer system further has a controller according to claim 1 for maneuvering in use said interrogation plane with respect to the reference surface.

14. A computer system for implementing the method according to claim 12, the computer system further including: a visual display for displaying said sectional image.

* * * * *